(12) United States Patent
Tanner, Jr. et al.

(10) Patent No.: US 10,535,431 B2
(45) Date of Patent: *Jan. 14, 2020

(54) SYSTEM AND METHOD FOR DYNAMIC SCHEDULE AGGREGATION

(71) Applicant: Change Healthcare Holdings, LLC, Nashville, TN (US)

(72) Inventors: Theodore Calhoun Tanner, Jr., San Mateo, CA (US); Thomas Dixon Whitmire, IV, San Mateo, CA (US); Timothy Scott Dunlevy, San Mateo, CA (US); Brian Scott Corbin, San Mateo, CA (US); Douglas Clark Thomas, San Mateo, CA (US)

(73) Assignee: Change Healthcare Holdings, LLC, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/941,423

(22) Filed: Nov. 13, 2015

(65) Prior Publication Data

US 2016/0078181 A1 Mar. 17, 2016

Related U.S. Application Data

(63) Continuation of application No. 14/608,085, filed on Jan. 28, 2015, now Pat. No. 10,007,757.

(60) Provisional application No. 62/051,739, filed on Sep. 17, 2014.

(51) Int. Cl.
*G16H 40/20* (2018.01)
(52) U.S. Cl.
CPC .................................. *G16H 40/20* (2018.01)

(58) Field of Classification Search
CPC ........ G06F 19/322; G06F 19/323–327; G06Q 50/22; G06Q 50/24; G06Q 10/1095
USPC ........................................................ 705/2, 3
See application file for complete search history.

(56) References Cited

U.S. PATENT DOCUMENTS

| | | | |
|---|---|---|---|
| 5,623,695 A * | 4/1997 | Lozinski ................... | G06F 9/44 707/999.1 |
| 5,872,021 A | 2/1999 | Matsumoto et al. | |
| 6,389,454 B1 * | 5/2002 | Ralston ................. | G06F 19/327 709/204 |
| 6,546,428 B2 | 4/2003 | Baber et al. | |
| 7,386,565 B1 | 6/2008 | Singh et al. | |
| 7,917,378 B2 | 3/2011 | Fitzgerald et al. | |
| 7,917,515 B1 | 3/2011 | Lemoine | |

(Continued)

FOREIGN PATENT DOCUMENTS

| | | |
|---|---|---|
| GB | 2478440 | 10/2013 |
| WO | WO2012/122065 | 9/2012 |

OTHER PUBLICATIONS

PCT International Search Report of PCT/US15/13613; dated May 14, 2015; (2 pgs.).

(Continued)

*Primary Examiner* — Jason S Tiedeman
(74) *Attorney, Agent, or Firm* — Meunier Carlin & Curfman LLC

(57) ABSTRACT

A scheduling system and method are provided. The system and method provide a mechanism for a customer to schedule appointments directly with healthcare providers which is not presently possible since each healthcare provider may use a different practice management system that has different formats and protocols.

17 Claims, 24 Drawing Sheets

SCHEDULE MULTIPLE APPOINTMENTS

(56) References Cited

U.S. PATENT DOCUMENTS

| | | | |
|---|---|---|---|
| 7,970,802 B2 | 6/2011 | Ishizaki | |
| 7,992,153 B2 | 8/2011 | Ban | |
| 8,046,778 B1 * | 10/2011 | Getlin | G06F 9/54 719/328 |
| 8,060,395 B1 * | 11/2011 | Frasher | G06Q 10/1093 705/7.18 |
| 8,073,801 B1 | 12/2011 | Von Halle et al. | |
| 8,095,975 B2 | 1/2012 | Boss et al. | |
| 8,103,667 B2 | 1/2012 | Azar et al. | |
| 8,103,952 B2 | 1/2012 | Hopp | |
| 8,203,562 B1 | 6/2012 | Alben et al. | |
| 8,229,808 B1 | 7/2012 | Heit | |
| 8,244,566 B1 * | 8/2012 | Coley | G06Q 10/109 705/7.11 |
| 8,286,191 B2 | 10/2012 | Amini et al. | |
| 8,359,298 B2 | 1/2013 | Schacher et al. | |
| 8,364,501 B2 | 1/2013 | Rana et al. | |
| 8,417,755 B1 | 4/2013 | Zimmer | |
| 8,495,108 B2 | 7/2013 | Nagpal et al. | |
| 8,515,777 B1 | 8/2013 | Rajasenan | |
| 8,719,068 B1 * | 5/2014 | Harding | G06Q 10/1095 705/2 |
| 8,817,665 B2 | 8/2014 | Thubert et al. | |
| 8,984,464 B1 | 3/2015 | Mihal et al. | |
| 9,165,045 B2 | 10/2015 | Mok et al. | |
| 9,208,284 B1 | 12/2015 | Douglass | |
| 9,367,350 B2 * | 6/2016 | Ringseth | G06F 9/45533 |
| 2002/0022973 A1 | 2/2002 | Sun et al. | |
| 2002/0038233 A1 | 3/2002 | Shubov et al. | |
| 2002/0120692 A1 * | 8/2002 | Schiavone | G06Q 10/107 709/206 |
| 2002/0156672 A1 * | 10/2002 | Burko | G06Q 10/063116 705/7.16 |
| 2002/0165738 A1 | 11/2002 | Dang | |
| 2003/0055668 A1 * | 3/2003 | Saran | G06F 9/465 705/301 |
| 2003/0061087 A1 * | 3/2003 | Srimuang | G06Q 10/06314 705/7.18 |
| 2003/0097359 A1 | 5/2003 | Ruediger | |
| 2003/0171953 A1 | 9/2003 | Narayanan et al. | |
| 2003/0217159 A1 | 11/2003 | Schramm-Apple et al. | |
| 2003/0220818 A1 * | 11/2003 | Lemchen | G06Q 30/02 705/2 |
| 2003/0233252 A1 | 12/2003 | Haskell et al. | |
| 2004/0143446 A1 | 7/2004 | Lawrence | |
| 2005/0010452 A1 | 1/2005 | Lusen | |
| 2005/0055252 A1 * | 3/2005 | Todd | G06Q 10/02 705/5 |
| 2005/0060348 A1 * | 3/2005 | Coyne | G06Q 10/10 |
| 2005/0071189 A1 | 3/2005 | Blake et al. | |
| 2005/0102170 A1 | 5/2005 | Lefever et al. | |
| 2005/0137912 A1 | 6/2005 | Rao et al. | |
| 2005/0152520 A1 | 7/2005 | Logue | |
| 2005/0182780 A1 | 8/2005 | Forman et al. | |
| 2005/0222912 A1 | 10/2005 | Chambers | |
| 2005/0234741 A1 * | 10/2005 | Rana | G06Q 10/107 705/2 |
| 2006/0004974 A1 * | 1/2006 | Lin | G06F 21/6245 711/164 |
| 2006/0026051 A1 * | 2/2006 | Rose | G06Q 10/10 705/80 |
| 2006/0036478 A1 * | 2/2006 | Aleynikov | G06Q 10/06 705/3 |
| 2006/0047554 A1 * | 3/2006 | Larsen | G06Q 10/06 705/7.24 |
| 2006/0074290 A1 | 4/2006 | Chen et al. | |
| 2006/0089862 A1 | 4/2006 | Anandarao et al. | |
| 2006/0122865 A1 * | 6/2006 | Preiss | G06Q 10/0633 705/2 |
| 2006/0129428 A1 | 6/2006 | Wennberg | |
| 2006/0136264 A1 | 6/2006 | Eaton et al. | |
| 2007/0113172 A1 | 5/2007 | Behrens et al. | |
| 2007/0118399 A1 | 5/2007 | Avinash et al. | |
| 2007/0156455 A1 | 7/2007 | Tarino et al. | |
| 2007/0174101 A1 | 7/2007 | Li et al. | |
| 2007/0180451 A1 | 8/2007 | Ryan et al. | |
| 2007/0214133 A1 | 9/2007 | Liberty et al. | |
| 2007/0233603 A1 | 10/2007 | Schmidgall et al. | |
| 2007/0260492 A1 | 11/2007 | Feied et al. | |
| 2007/0276858 A1 | 11/2007 | Cushman et al. | |
| 2007/0288262 A1 | 12/2007 | Sakaue et al. | |
| 2008/0013808 A1 | 1/2008 | Russo et al. | |
| 2008/0082980 A1 * | 4/2008 | Nessland | G06Q 10/02 718/104 |
| 2008/0091592 A1 | 4/2008 | Blackburn et al. | |
| 2008/0109262 A1 * | 5/2008 | Dvorak | G06F 19/3418 705/3 |
| 2008/0126264 A1 | 5/2008 | Tellefsen et al. | |
| 2008/0133436 A1 | 6/2008 | Di Profio | |
| 2008/0215993 A1 * | 9/2008 | Rossman | G06Q 10/00 715/753 |
| 2008/0288292 A1 | 11/2008 | Bi et al. | |
| 2008/0295094 A1 | 11/2008 | Korupolu et al. | |
| 2008/0319983 A1 | 12/2008 | Meadows | |
| 2009/0083664 A1 | 3/2009 | Bay | |
| 2009/0125796 A1 | 5/2009 | Day et al. | |
| 2009/0192864 A1 | 7/2009 | Song et al. | |
| 2009/0198520 A1 | 8/2009 | Piovanetti-Perez | |
| 2009/0300054 A1 | 12/2009 | Fisher et al. | |
| 2009/0307104 A1 | 12/2009 | Weng | |
| 2009/0313045 A1 | 12/2009 | Boyce | |
| 2010/0017222 A1 * | 1/2010 | Yeluri | G06Q 10/06 705/2 |
| 2010/0070303 A1 * | 3/2010 | Massoumi | G06Q 10/109 705/3 |
| 2010/0076950 A1 | 3/2010 | Kenedy et al. | |
| 2010/0082620 A1 | 4/2010 | Jennings, III et al. | |
| 2010/0088108 A1 | 4/2010 | Machado | |
| 2010/0088119 A1 | 4/2010 | Tipirneni | |
| 2010/0138243 A1 | 6/2010 | Carroll | |
| 2010/0217973 A1 | 8/2010 | Kress et al. | |
| 2010/0228564 A1 * | 9/2010 | Kharraz Tavakol | G06F 19/328 705/2 |
| 2010/0228721 A1 | 9/2010 | Mok et al. | |
| 2010/0295674 A1 | 11/2010 | Hsieh et al. | |
| 2010/0332273 A1 | 12/2010 | Balasubramanian et al. | |
| 2011/0009707 A1 * | 1/2011 | Kaundinya | G06F 19/3418 600/300 |
| 2011/0015947 A1 | 1/2011 | Erry et al. | |
| 2011/0055252 A1 | 3/2011 | Kapochunas et al. | |
| 2011/0071857 A1 | 3/2011 | Malov et al. | |
| 2011/0137672 A1 | 6/2011 | Adams et al. | |
| 2011/0218827 A1 | 9/2011 | Kennefick et al. | |
| 2011/0270625 A1 | 11/2011 | Pederson et al. | |
| 2012/0004943 A1 * | 1/2012 | Reichman | G06Q 10/06314 705/7.24 |
| 2012/0011029 A1 | 1/2012 | Thomas | |
| 2012/0035984 A1 | 2/2012 | Srinivasa et al. | |
| 2012/0078940 A1 | 3/2012 | Kolluri et al. | |
| 2012/0130736 A1 | 5/2012 | Dunston et al. | |
| 2012/0158429 A1 | 6/2012 | Murawski et al. | |
| 2012/0158750 A1 | 6/2012 | Faulkner et al. | |
| 2012/0173279 A1 * | 7/2012 | Nessa | G06Q 10/063118 705/3 |
| 2012/0245958 A1 | 9/2012 | Lawrence et al. | |
| 2012/0246727 A1 | 9/2012 | Elovici et al. | |
| 2012/0290320 A1 | 11/2012 | Kurgan et al. | |
| 2012/0290564 A1 | 11/2012 | Mok et al. | |
| 2013/0030827 A1 | 1/2013 | Snyder et al. | |
| 2013/0044749 A1 | 2/2013 | Eisner et al. | |
| 2013/0085769 A1 | 4/2013 | Jost et al. | |
| 2013/0138554 A1 | 5/2013 | Nikankin et al. | |
| 2013/0166552 A1 | 6/2013 | Rozenwald et al. | |
| 2013/0204940 A1 | 8/2013 | Kinsel et al. | |
| 2013/0290007 A1 * | 10/2013 | Haq | G06Q 50/22 705/2 |
| 2013/0304903 A1 | 11/2013 | Mick et al. | |
| 2014/0046931 A1 | 2/2014 | Mok et al. | |
| 2014/0056243 A1 | 2/2014 | Pelletier et al. | |
| 2014/0059084 A1 | 2/2014 | Adams et al. | |

(56) References Cited

U.S. PATENT DOCUMENTS

| | | | |
|---|---|---|---|
| 2014/0088981 A1 | 3/2014 | Momita | |
| 2014/0136233 A1 | 5/2014 | Atkinson et al. | |
| 2014/0207509 A1* | 7/2014 | Yu | G06Q 10/1095 705/7.19 |
| 2014/0222482 A1* | 8/2014 | Gautam | G06Q 10/1095 705/7.19 |
| 2014/0244300 A1 | 8/2014 | Bess et al. | |
| 2014/0249878 A1* | 9/2014 | Kaufman | G06Q 10/1095 705/7.19 |
| 2014/0278491 A1 | 9/2014 | Weiss | |
| 2014/0358578 A1 | 12/2014 | Ptachcinski | |
| 2014/0358845 A1* | 12/2014 | Mundlapudi | G06F 17/30563 707/602 |
| 2015/0095056 A1 | 4/2015 | Ryan et al. | |
| 2015/0112696 A1* | 4/2015 | Kharraz Tavakol | G06Q 10/06311 705/2 |
| 2015/0142464 A1 | 5/2015 | Rusin et al. | |
| 2015/0142495 A1* | 5/2015 | Garakani | G06Q 10/1095 705/7.19 |
| 2015/0154528 A1* | 6/2015 | Kharraz Tavakol | G06Q 10/0631 705/2 |
| 2015/0199482 A1 | 7/2015 | Corbin et al. | |
| 2015/0332283 A1 | 11/2015 | Witchey | |
| 2016/0028552 A1 | 1/2016 | Spanos et al. | |
| 2016/0055205 A1 | 2/2016 | Jonathan et al. | |
| 2016/0253679 A1 | 9/2016 | Venkatraman et al. | |
| 2016/0328641 A1 | 11/2016 | Alsaud et al. | |
| 2016/0342750 A1 | 11/2016 | Alsaud et al. | |
| 2016/0342751 A1 | 11/2016 | Alsaud et al. | |
| 2017/0091397 A1 | 3/2017 | Shah et al. | |
| 2017/0103164 A1 | 4/2017 | Dunlevy et al. | |
| 2017/0103165 A1 | 4/2017 | Dunlevy et al. | |
| 2017/0132621 A1 | 5/2017 | Miller et al. | |

OTHER PUBLICATIONS

PCT Written Opinion of the International Searching Authority of PCT/US15/13613; dated May 14, 2015; (5 pgs.).
Ahlswede et al., *Network Information Flow*, IEEE Transactions on Information Theory, vol. 46, No. 4; Jul. 2000 (13 pgs.).
Bhattacharya, Indrajit and Getoor, Lise, *Entity Resolution in Graphs*, Department of Computer Science, University of Maryland (2005) (21 pgs.).
Chen et al., *Adaptive Graphical Approach to Entity Resolution*, Jun. 18-23, 2007, Proceedings of the 7th ACM/IEEE-CS Joint Conference on Digital Libraries, pp. 204-213 (10 pgs.).
Christen, *Data Matching, Concepts and Techniques for Record Linkage, Entity Resolution, and Duplicate Detection*, © Springer-Verlag Berlin Heidelberg, 2012 (279 pgs.).
Cohen et al., *A Comparison of String Metrics for Matching Names and Records*, © 2003, American Association for Artificial Intelligence (www.aaai.org) (6 pgs.).
Coleman et al., *Medical Innovation—a diffusion study*; The Bobbs-Merrill Company, Inc., 1966 (248 pgs.).
Domingos et al., *Mining High-Speed Data Streams*, (2000) (10 pgs.).
Greenhalgh et al., *Diffusion of Innovations in Health Service Organisations—a systematic literature review*, Blackwell Publishing, 2005 (325 pgs.).
Jackson et al., *The Evolution of Social and Economic Networks*, Journal of Economic Theory 106, pp. 265-295, 2002 (31 pgs.).
Jackson, Matthew O., *Social and Economic Networks*, Princeton University Press, 2008 (509 pgs.).
Krempl et al., *Open Challenges for Data Stream Mining Research*, SIGKDD Explorations, vol. 16, Issue 1, Jun. 2014 (64 pgs.).
Rebuge, *Business Process Analysis in Healthcare Environments*, 2011, Ellsevier Ltd., pp. 99-116 (18 pgs.).
Wasserman et al., *Social Network Analysis: Methods and Applications*, Cambridge University Press; 1994 (434 pgs.).
White et al., *Algorithms for Estimating Relative Importance in Networks*, Proceedings of the Ninth ACM SIGKDD International Conference on Knowledge Discovery and Data Mining, 2003 (10 pgs.).
(Mathjax), *Naive Bayes Categorisation (with some help from Elasticsearch)*, blog post dated Dec. 29, 2013 (https://blog.wtf.sg/2013/12/29/naive-bayes-categorisation-with-some-help-from-elasticsearch/). (8 pgs.).
Webpage: New Health Care Electronic Transactions Standards Versions 5010, D.0, and 3.0, Jan. 2010 ICN 903192; http://www.cms.gov/Regulations-and-Guidance/HIPAA-Adminstrative-Simplification/Versions5010andD0/downloads/w5010BasicsFctCht.pdf (4 pgs.).
Webpage: U.S. Dept. of Health and Human Services, Guidance Regarding Methods for De-identification of Protected Health Information in Accordance with the Health Insurance Portability and Accountability Act (HIPAA) Privacy Rule, http://www.hhs.gov/ocr/privacy/hipaa/understanding/coveredentities/De-identification/guidance.html printed Oct. 15, 2015 (14 pgs.).
Anonymous: "Oauth—Wikipedia", Sep. 23, 2013. Retrieved from the Internet URL:https://en.wikipedia.org/w/index.php?title+oAuth&oldid+574187532.
Lin et al., A simplicial complex, a hypergraph, structure in the latent semantic space of document clustering, © 2005 Elsevier Inc. (26 pgs.).
Anonymous: "Oauth" Wikipedia—Retrieved from the Internet URL:https://en.wikipedia.org/wiki/Oauth (8 pgs.).
Version 5010 and D.O, Center for Medicare & Medicaid Services (1 page).

* cited by examiner

GET Endpoint:

| /schedule/schedulers/ |
|---|

Response:

```
{
  [
     scheduler_id: <politdok unique id for the scheduling system>,
     scheduler_description:<The third party scheduling system>
  ]}
```

FIGURE 2A

GET Endpoint:

/schedule/appointmenttypes/

Response:

```
{
  [
     appointment_type_id:◇,
     appointment_type_description:◇
  ]
}
```

FIGURE 2B

GET Endpoint:
{id} is the PokitDok provider id

/schedule/provider/{id}

Response:

```
{
   supported_methods:[<one or more of: open_slots, book_
appointment, update_appointment,
      cancel_appointment>],
   supported_appointment_types: [<one or more appointment type
ids, see appointment type
         method>],
   scheduler_id:<>,
}
```

FIGURE 2C

PUT Endpoint:

```
/schedule/provider/
```

Request Body:

```
{
   pd_provider_schedule_id: <pokitdok id for the providers schedule instance>,
   pd_provider_schedule_caldav: <CalDAV resource name>
}
```

Response:

```
{
   pd_provider_id: <pokitdok provider id for location>,
   supported_methods: [<one or more of: open_slots, book_appointment, update_appointment,
            cancel_appointment>],
   supported_appointment_types: [<one or more appointment type ids, see appointment type
            method>],
   scheduler_id: <pokitdok id for the supported scheduling system>,
   scheduler_attributes: {...}
}
```

FIGURE 2D

POST Endpoint:

/schedule/slots/

Request Body:

```
{
  [{
    location:<>,
    pd_provider_id:<PokitDok provider id for location>,
    [slot:{id:<>, pd_provider_id:<PokitDok provider id for open slot>, timespan:<>}],
    appointment_type_id:<>
  }]
{
```

Response:

HTTP Status Code 200 on Success

FIGURE 2E

GET Endpoint:
{id} is the PokitDok provider id

/schedule/appointments/{id}

Query Parameters:

| NAME | TYPE | DESCRIPTION |
|---|---|---|
| BOOKED | STRING | FALSE TO RETURN OPEN SLOTS, TRUE TO RETURN BOOKED APPOINTMENTS, NONE TO RETURN SLOTS AND APPOINTMENTS. |
| APPOINTMENT_TYPE | STRING | THE POKITDOK DEFINED APPOINTMENT TYPE |
| START_DATE | STRING | ISO 8601 DATE AND TIME |
| END_DATE | STRING | ISO 8601 DATE AND TIME |

Response:

```
{
  [{
     location:<>,
     pd_provider_id:<PokitDok provider id for location>,
     [slot:{id:<>, pd_provider_id:<PokitDok provider id for open slot>, timespan:<>}]
  }]
}
```

FIGURE 2F

POST Endpoint:

/schedule/appointments/

Request Body:

```
{[
   location:<>,
   pd_provider_id:<pokitdok provider id for location>,
   slot_id<>,
   attributes:{
      callback: <optional, http url for posting appointment events to>,
      consumer: {
         id: <pokitdok consumer id (marketplace)>,
         email: <email address>,
         phone: <home phone #>,
         birth_date: <>,
         name: {
            last: <>,
            first: <>
         },
         ...
      },
      ...
   },
]}
```

FIGURE 2G

Response:

```
{[
   appointment_id<>,
   attributes: {...}
]}
```

FIGURE 2H

PUT Endpoint:

/schedule/appointments/

Request Body:

```
{[
   appointment_id:◇,
   attributes: {...}
]}
```

Response Body:

```
{[
   appointment_id:◇,
   attributes: {...}
]}
```

FIGURE 2I

DELETE Endpoint:

/schedule/appointments/

Request Body:

```
{[
    appointment_id:<>
]}
```

Response:

HTTP Status Code 200 on Success

FIGURE 2J

| Object | Definition |
|---|---|
| Process | A collection of steps that are executed in sequence by the process. |
| Step | Executes actions in a sequence, collects results for processing by the reducer. |
| Action | Programmatic methods (functions) to generate results and optional side effects. |
| Result | Output data from an action or reducer that can be used as input to a step. |
| Reducer | Analyses results and generates a single output and optionally directs as input to a step. |
| Side Effect | Intended effect in an external system. |

FIGURE 3A

| Subject | Object | Predicate |
|---|---|---|
| Process | is-composed-of | Step(s) |
| Step | executes | Action(s) |
| Step | has-closure | Reducer |
| Action | expects-a | Result |
| Action | creates-a | Result |
| Reducer | directs-to | Step |
| Reducer | creates-a | Step |

FIGURE 3B

| Object Type | Instance Name | Description |
|---|---|---|
| Process | Book_Appointment | Book an appointment |
| Step | Get_Providers | Step to get providers by given attributes, i.e. speciality and location |
| Action | Query_Providers | Query providers by speciality location |
| Result | Provider_List | List of providers |
| Reducer | Provider_Filter | Filter for providers with scheduling capability |
| Step | Get_Availability | Step to query provider availability |
| Action | Query_Slots | For each provider input, query provider specific scheduler for availability for an appointment type in given timespan |
| Result | Open_Slots | List of available appointment slots |

FIGURE 4B

| Object Type | Instance Name | Description |
|---|---|---|
| Reducer | Slot_Reduce | Sort Open_Slots result by location closeness and availability and return topmost result slot |
| Result | Open_Slot | Best fit available slots |
| Step | Book_Slot | Step to reserve the open slot and publish to the PokitDok calendar server |
| Action | Schedule_Appointment | Translate the open slot into a scheduler specific call to reserve the appointment |
| Result | Appointment_Scheduled | Scheduler response confirming appointment |
| Action | Publish_Appointment | Publish the appointment to the consumer's calender on the PokitDok calendar server |
| Result | Appointment_Published | PokitDok calendar response confirming appointment |
| Reducer | Appointment_Booked | Confirms appointment scheduled and published |
| Result | Booked_Appointment | Appointment details document |

FIGURE 4C

| Subject | Predicate | Object |
|---|---|---|
| Book_Appointment | is-composed-of | Get_Providers |
| Book_Appointment | is-composed-of | Get_Availability |
| Book_Appointment | is-composed-of | Book_Slot |
| Get_Providers | executes | Query_Providers |
| Query_Providers | expects-a | Provider_List |
| Query_Providers | creates-a | Provider_List |
| Provider_Filter | creates-a | Provider_List |
| Provider_Filter | directs-to | Get_Availability |
| Provider_List | inputs-to | Get_Availability |

FIGURE 4D

| Subject | Predicate | Object |
|---|---|---|
| Get_Availability | executes | Query_Slots |
| Query_Slots | expects-a | Open_Slots |
| Query_Slots | creates-a | Open_Slots |
| Slot_Reduce | creates-a | Open_Slot |
| Slot_Reduce | directs-to | Book_Slot |
| Open_Slot | inputs-to | Book_Slot |
| Book_Slot | executes | Schedule_Appointment |
| Schedule_Appointment | expects-a | Appointment_Scheduled |
| Schedule_Appointment | creates-a | Appointment_Scheduled |
| Book_Slot | executes | Publish_Appointment |
| Publish_Appointment | expects-a | Appointment_Published |
| Publish_Appointment | creates-a | Appointment_Published |
| Appointment_Booked | creates-a | Booked_Appointment |

FIGURE 4E

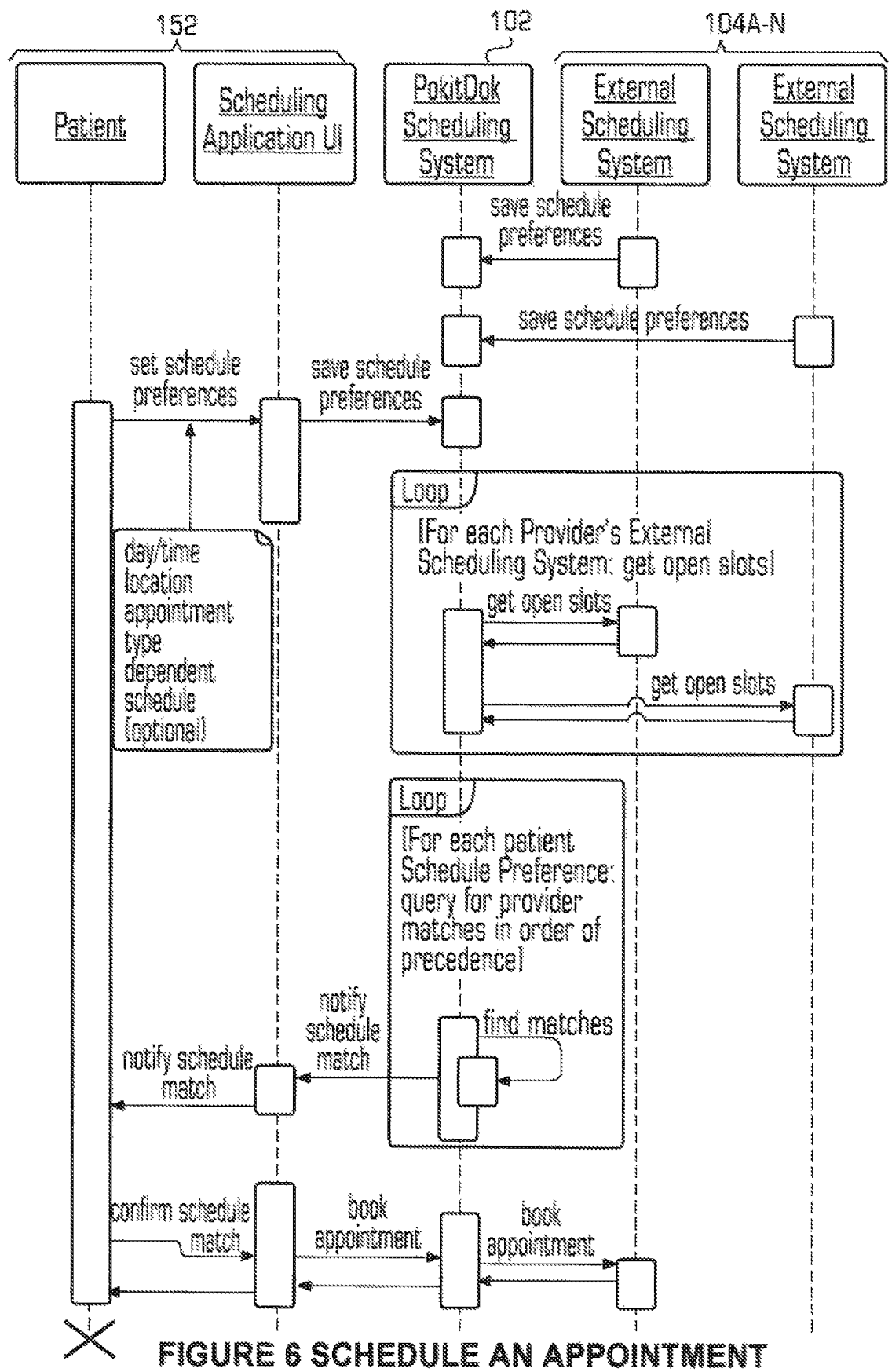
FIGURE 6 SCHEDULE AN APPOINTMENT

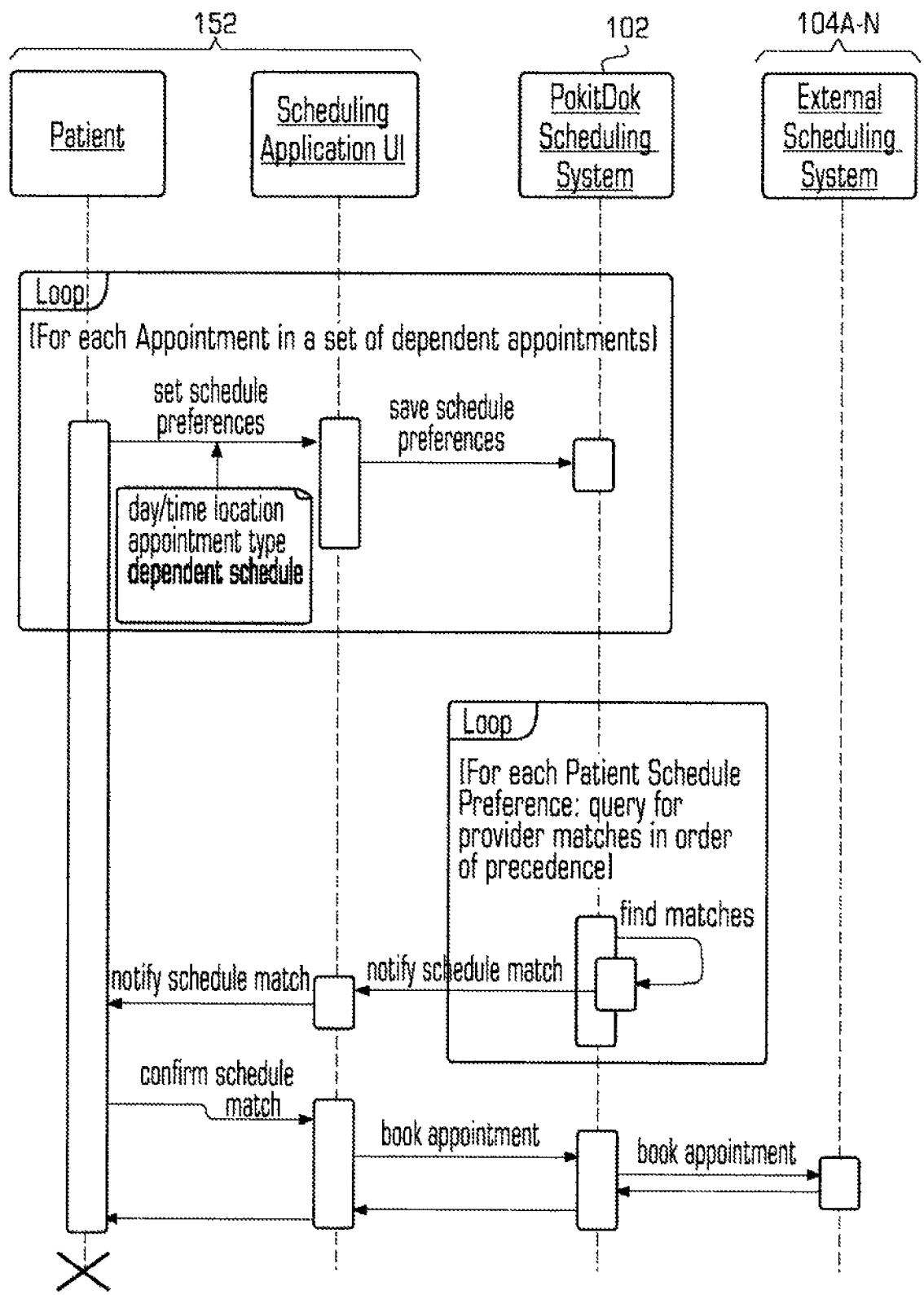
FIGURE 7 SCHEDULE MULTIPLE APPOINTMENTS

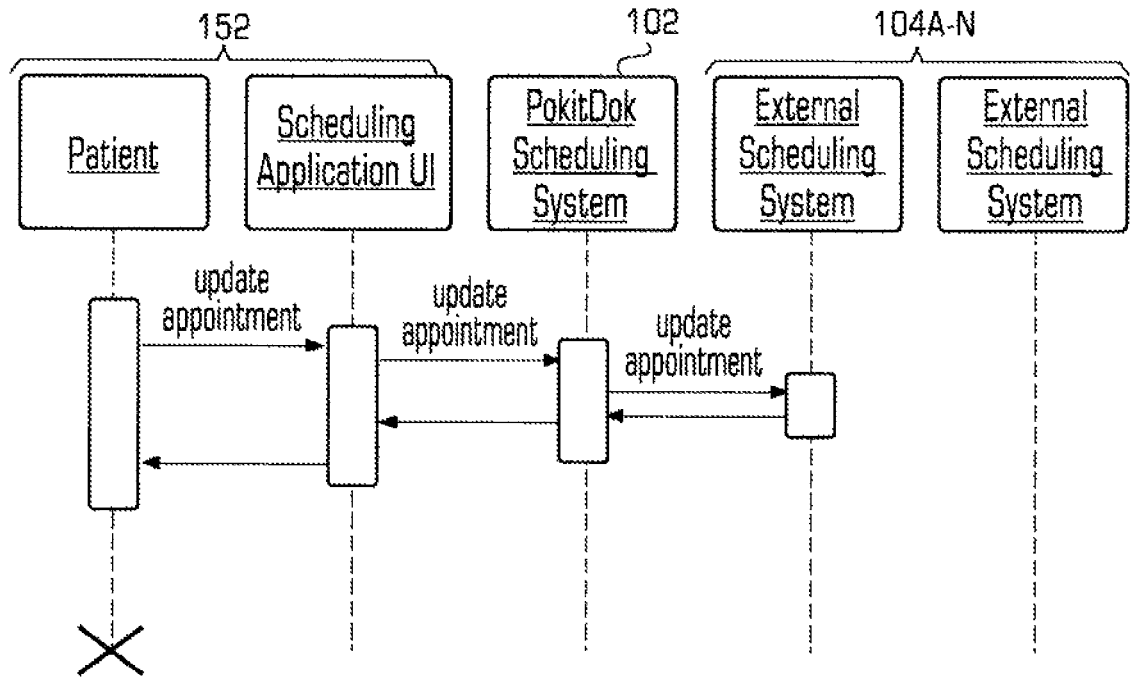
FIGURE 8 UPDATE APPOINTMENT
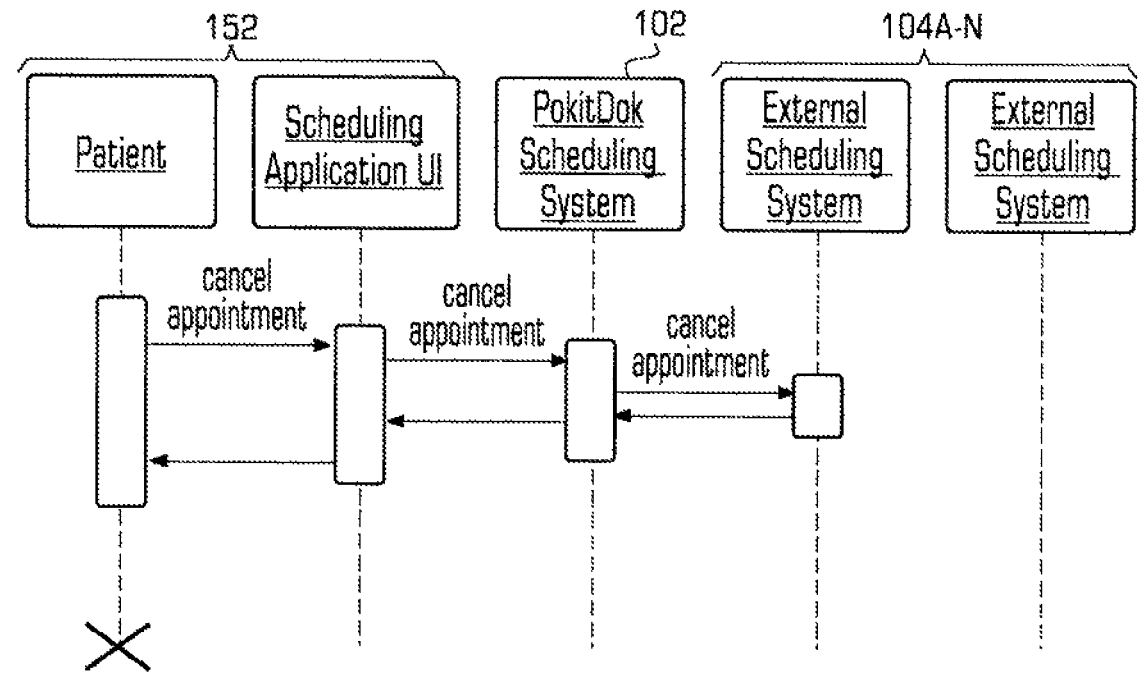
FIGURE 9 CANCEL APPOINTMENT

SYSTEM AND METHOD FOR DYNAMIC SCHEDULE AGGREGATION

PRIORITY CLAIM

This application is a continuation of and claims priority under 35 USC 120 to U.S. patent application Ser. No. 14/608,085, filed on Jan. 28, 2015 and entitled "System and Method for Dynamic Schedule Aggregation" which in turn claims the benefit under 35 USC 119(e) and priority under 35 USC 120 to U.S. Provisional Patent Application Ser. No. 62/051,739, filed on Sep. 17, 2014 and entitled "System and Method for Dynamic Schedule Aggregation", the entirety of all of which are incorporated herein by reference.

FIELD

The disclosure relates generally to a system and method of healthcare service scheduling.

BACKGROUND

Healthcare providers and practices utilize practice management (PM) systems to perform mission critical healthcare processes such as billing, reporting, and appointment scheduling. In general, the PM system appointment scheduling interfaces are proprietary and do not share any common interfaces or common data. This disparity presents several challenges in creating consumer centric views of scheduling data, as healthcare providers may utilize separate PM systems whose data and operations are not interchangeable. Thus, it is desirable to provide a scheduling system that provides scheduling across the various PM scheduling systems and it is to this end that the disclosure is directed.

BRIEF DESCRIPTION OF THE DRAWINGS

FIGS. 2A-2J illustrate examples of a set of operations supported by the scheduling system in FIGS. 1A and 1B;
FIGS. 3A-3C illustrate a workflow vocabulary of a scheduling method that may be implemented by the system in FIGS. 1A and 1B;
FIGS. 4A-4E illustrate a method for scheduling a single appointment workflow that may be implemented by the system in FIGS. 1A and 1B;
FIG. 6 illustrates an example of a workflow for scheduling an appointment;
FIG. 7 illustrates an example of a workflow for scheduling multiple appointments;
FIG. 8 illustrates an example of a workflow for updating an appointment;
and
FIG. 9 illustrates an example of a workflow for cancelling an appointment.

DETAILED DESCRIPTION OF ONE OR MORE EMBODIMENTS

The disclosure is particularly applicable to a healthcare service scheduling system with aggregated scheduling using a client server type computer architecture and it is in this context that the disclosure will be described. It will be appreciated, however, that the scheduling system and method may be used with other healthcare systems in which it is desirable to be able to schedule appointments. In addition, the scheduling system and method described below may be leveraged and incorporated into the PokItDok marketplace arbitrage system and method described in U.S. patent application Ser. No. 14/328,591, filed Jul. 10, 2014 (incorporated herein by reference) or into the PokItDok transaction data streaming system and method described in U.S. patent application Ser. No. 14/466,907, filed Aug. 22, 2014 (incorporated herein by reference.)

The scheduling system and method provides a mechanism for a customer to schedule appointments directly with healthcare providers which is not presently possible since each healthcare provider may use a different practice management system that has different formats and protocols. The scheduling system and method provides a scheduling aggregation system that addresses these issues by providing a scheduling engine which maps the system's data types and operations to the proprietary practice management ("PM") interfaces. The scheduling aggregation system provides consumers with access to provider's scheduling data in a uniform manner, regardless of the provider's PM system. This access allows the consumer to schedule an appointment with a specific health provider, view available appointments across multiple providers, and schedule multiple appointments with different providers for complex procedures. Leveraging this system within the healthcare market place system allows us to augment provider search results with scheduling information, and include scheduling operations within a business transaction.

The scheduling system supports the following use cases:
Fulfilling a scheduling request for a patient, in a single step, given a specific set of attributes such as location, specialty, and availability. The patient can specify the optimal time or location and the system will respond with respect to these parameters in an optimal fashion.
Fulfilling a complex scheduling request for a patient, consisting of multiple appointments which may involve different locations and healthcare providers.
Reserving appointments for high-volume resale use using parameters such as appointment type, location, and analytic trends which indicate which appointments have been most popular given an appointment type and location.

Figure 4A:
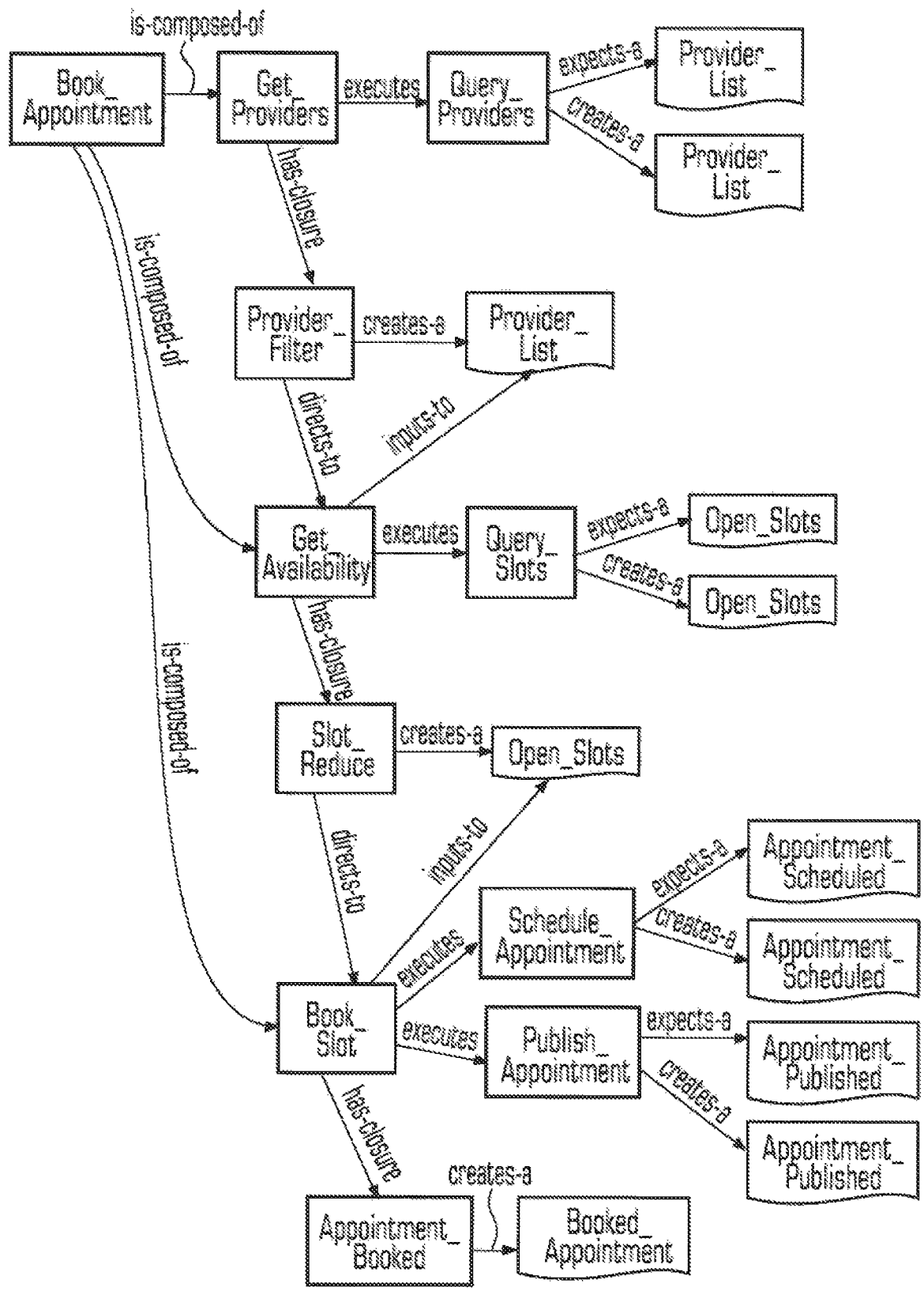
Figure 5:
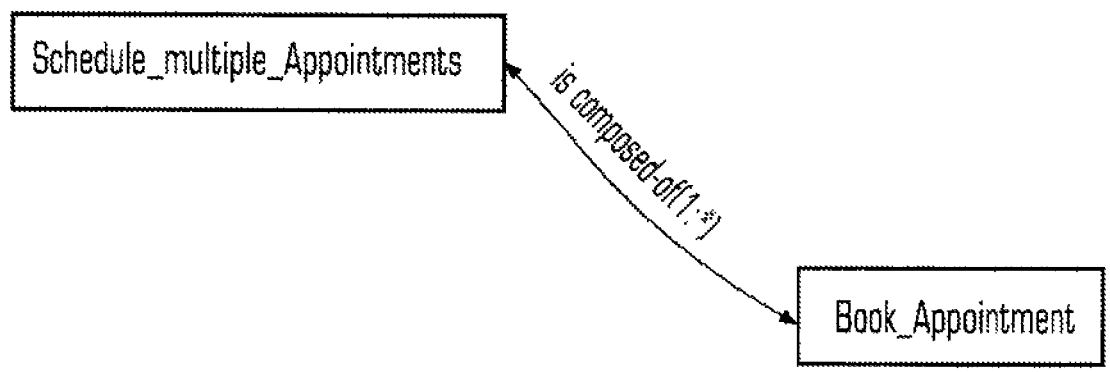
FIG. 5 illustrates a multiple appointment booking graph model that may be implemented by the system in FIGS. 1A and 1B.

A workflow for the single appointment reservation is illustrated in FIG. 4A and described below and that workflow is mapped to the workflow vocabulary in FIGS. 4B-4E as described below. The first use case, the single appointment reservation, is the basis for the remaining two use cases. The remaining use cases simply execute this base case N times where N is the number of appointment reservations requested for the use case. FIG. 5 illustrates the relationship between the Schedule_Multiple_Appointments process and Book_Appointment workflows.

Figure 1A:
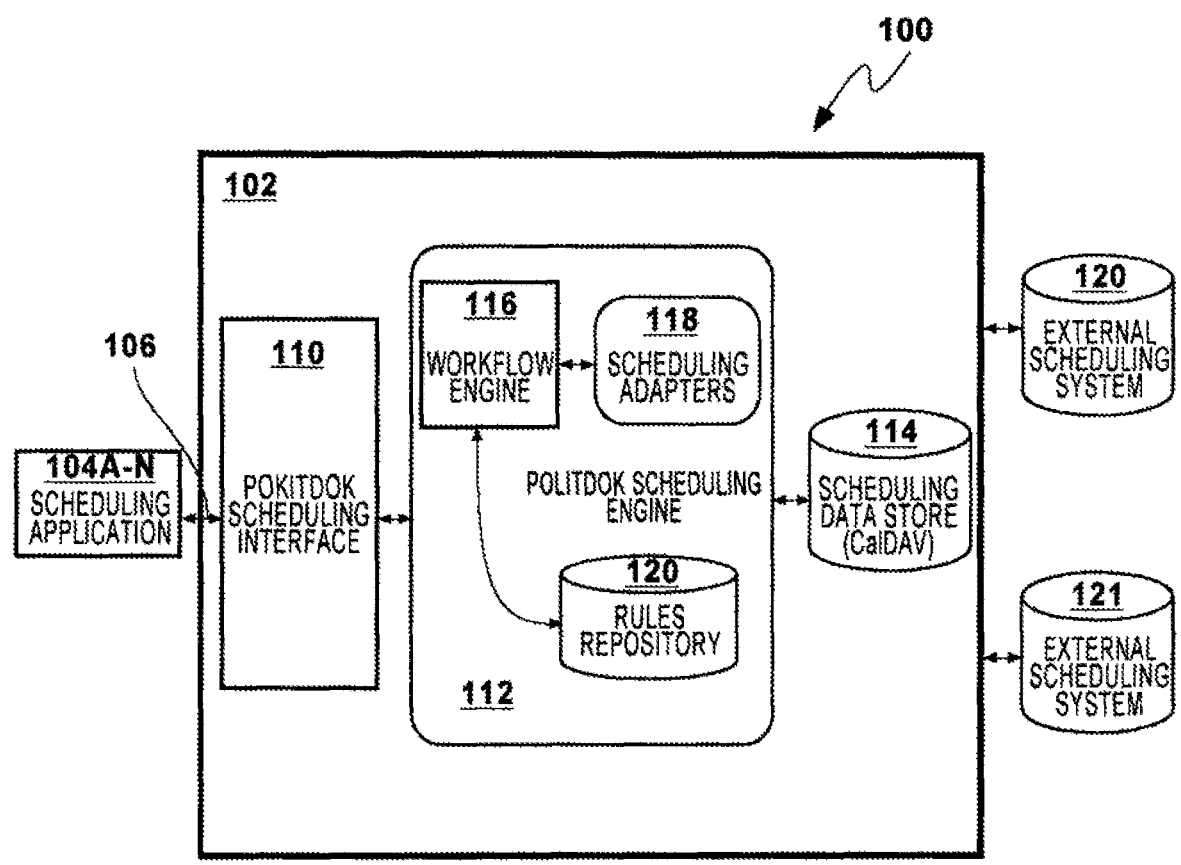
FIG. 1A illustrates a healthcare scheduling system.

FIG. 1A illustrates a healthcare scheduling system 100 that has a backend component 102 that may interface with a plurality of scheduling systems 120, 121 (that each have a scheduling application 104A-N) wherein each scheduling system has its own data formats, application programming interfaces (APIs) and the like. Each scheduling system may be a computer based system that has an API to access scheduling data. The backend component 102 (and each of its components as described below) may be implemented in software or hardware. When the components of the system are implemented in software, each component may be a plurality of lines of computer code that may be executed on a processor of a computing resource and stored in a memory of a computing resource to implement the functions and operations of the scheduling system. The computing resources may be one or more server computers or one or more cloud computing resources used by the system to store and execute the plurality of lines of code. When the components of the system are implemented in hardware, each component may be implemented as a microcontroller, a processor configured to perform certain operations, a programmable logic device, an application specific integrated circuit and the like. Alternatively, the scheduling components may be part of the software or hardware implemented PokItDok marketplace arbitrage system and method or the PokItDok transaction data streaming system and method and may utilize the hardware of those systems to implement the operations and processes of the scheduling system.

Each scheduling application is not part of the system since it is an external application, but is a consumer of a set of Scheduling Interfaces 110 of the system over a link 106, such as the Internet. The scheduling application utilizes the PokItDok Scheduling Interfaces to execute operations such as viewing open appointments, booking appointments, etc. The PokItDok Scheduling Interface 110 defines the system's supported operations, providing an entry point into the system for scheduling applications and clients. The PokitDok Scheduling Interface 110 may be an aggregate API meaning that it can interface with the variety of different APIs of each scheduling system. The API's data and operations are mapped to PM operations within a PokItDok Scheduling Engine 112. This abstraction allows client applications (104A-N) to schedule appointments in a uniform manner for all providers, without concern for the provider's PM system. For example, the scheduling system 120 may have an API based on transmission of HL7 formatted files over FTP, simultaneously the scheduling system 121 may have an API based on proprietary SOAP messages over HTTP, however the Scheduling Applications (104A-N) only need to implement the PokItDok Scheduling Interface 110 to schedule within all connected scheduling systems, such as 120 and 121 in this example.

The scheduling system 102 may further comprise the PokitDok Scheduling Engine 112 that maps data and operations from the PokItDok Scheduling Interfaces 110 to PM specific operations using a dynamic workflow process. The PokItDok Scheduling Engine 112 is the system's data conduit and all incoming and outgoing operations flow through the scheduling engine. The PokItDok Scheduling Engine 112 may further comprise the following components: 1) a set of scheduling adapters 118 that are a set of software components where a single scheduling adapter encapsulates the supported scheduling operations for a specific PM system; 2) a rules repository 120 that is a graph database that stores the meta-data, or rules, required to execute a process within the workflow engine. These rules define the steps and actions taken to complete a scheduling process; and 3) a workflow engine 116 that may load rules from the rules repository based on input received from the PokitDok Scheduling Interfaces 110. The workflow engine 116 uses the interface input to determine which rule sets and scheduling adapter are loaded. A workflow process is generated from the loaded rule sets and executed using the scheduling adapter. The system also may have a scheduling data store 114 that may be implemented using a CalDAV compliant server that may store the scheduling data of the system. The PokItDok Scheduling Engine 112 may be the central component of the system, providing data and operation mapping from the PokItDok Scheduling Interface to a PM scheduling adapter.

Figure 1B:
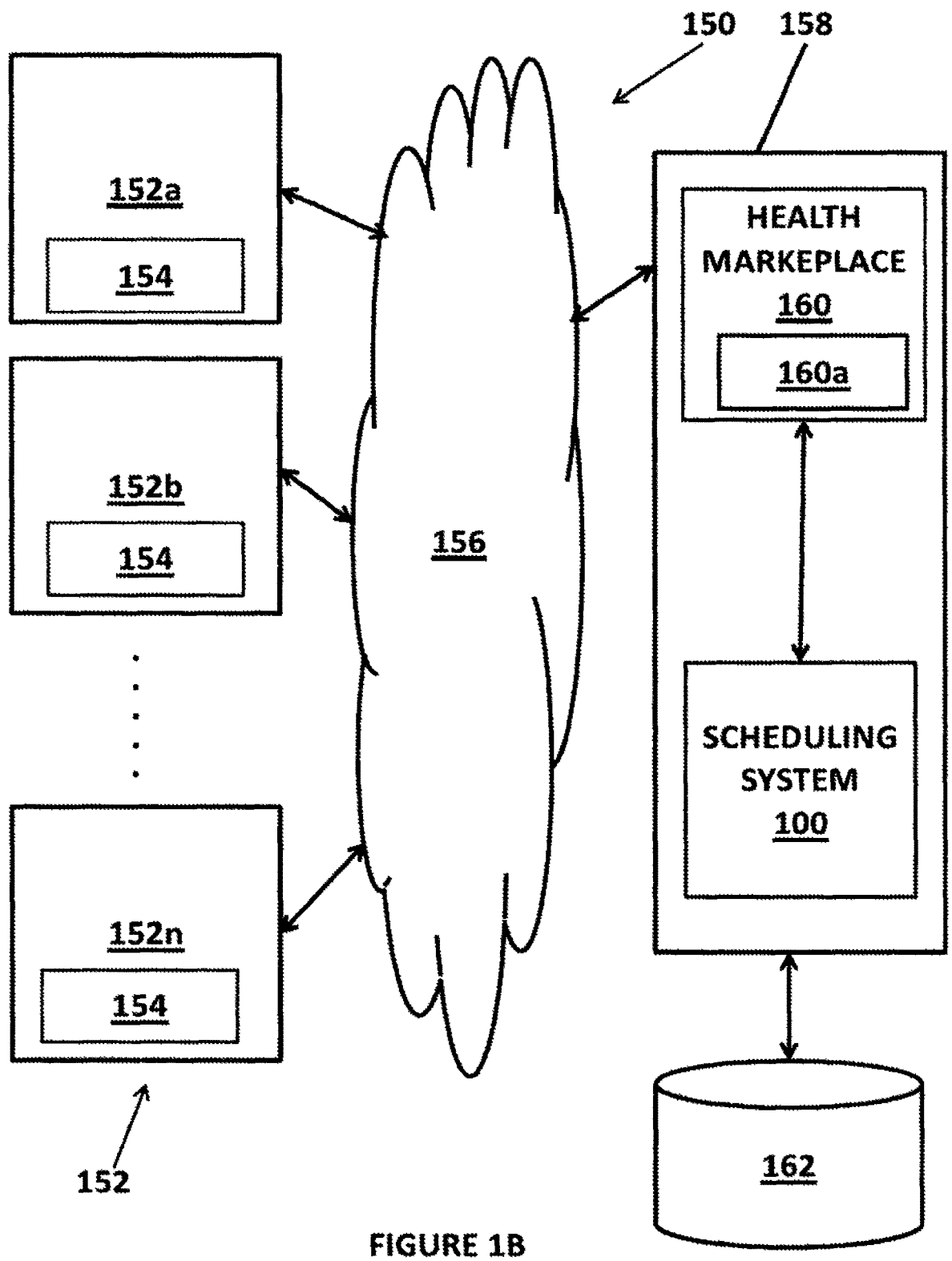
FIG. 1B illustrates a health services system that may incorporate the healthcare scheduling system.

FIG. 1B illustrates a health services system 150 that may incorporate the healthcare scheduling system 100. The health services system 150 may have one or more computing devices 152 that connect over a communication path 156 to a backend system 158. Each computing device 152, such as computing devices 152a, 152b, 152n as shown in FIG. 1B, may be a processor based device with memory, persistent storage, wired or wireless communication circuits and a display that allows each computing device to connect to and couple over the communication path 156 to a backend system 158. For example, each computing device may be a smartphone device, such as an Apple Computer product, Android OS based product, etc., a tablet computer, a personal computer, a terminal device, a laptop computer and the like. In one embodiment shown in FIG. 1B, each computing device 152 may store an application 154 in memory and then execute that application using the processor of the computing device to interface with the backend system. For example, the application may be a typical browser application or may be a mobile application. The communication path 106 may be a wired or wireless communication path that uses a secure protocol or an unsecure protocol. For example, the communication path 106 may be the Internet, Ethernet, a wireless data network, a cellular digital data network, a WiFi network and the like.

The backend system 158 may have a health marketplace engine 160 and the scheduling system 100 that may be coupled together. Each of these components of the backend system may be implemented using one or more computing resources, such as one or more server computers, one or more cloud computing resources and the like. In one embodiment, the health marketplace engine 160 and the health scheduling system 100 may each be implemented in software in which each has a plurality of lines of computer code that are executed by a processor of the one or more computing resources of the backend system. Thus, in that embodiment, the processor of the one or more computing resources of the backend system is configured to perform the operations and functions of the marketplace and health lending system as described below. In other embodiments, each of the health marketplace engine 160 and the health scheduling system 100 may be implemented in hardware such as a programmed logic device, a programmed processor or microcontroller and the like. The backend system 158 may be coupled to a store 162 that stores the various data and software modules that make up the healthcare system and the health lending system. The store 162 may be implemented as a hardware database system, a software database system or any other storage system.

The health marketplace engine 160 may allow practitioners that have joined the healthcare social community to reach potential clients in ways unimaginable even a few years ago. In addition to giving practitioners a social portal with which to communicate and market themselves with consumers, the marketplace gives each healthcare practitioner the ability to offer their services in an environment that is familiar to users of Groupon, Living Social, or other social marketplaces. The health scheduling system 100, as described above, may be used to schedule appointments for the health care system and the marketplace shown in FIG. 1B. Examples of the various scheduling actions for an appointment using the system in FIGS. 1A and 1B are described below with reference to FIGS. 6-9.

Figure 2H:
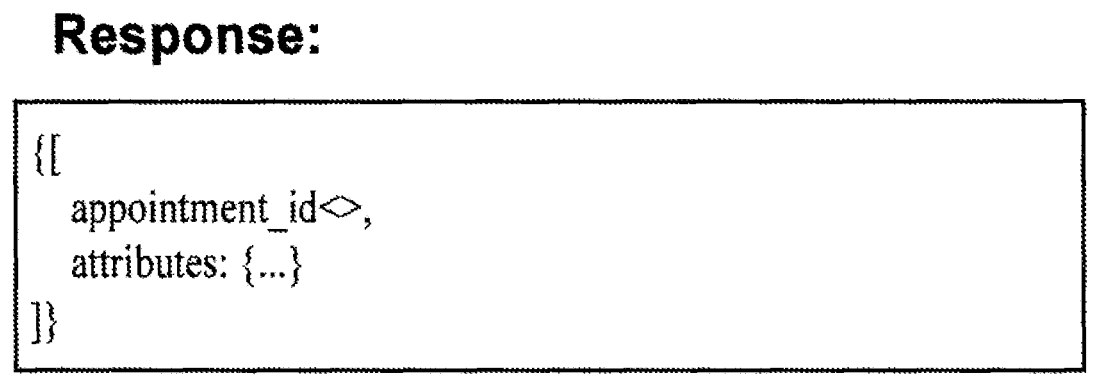

FIGS. 2A-2J illustrate examples of a set of operations supported by the scheduling system in FIGS. 1A and 1B and more particularly, these figures show the set of operations that may be supported by the scheduling interfaces 110 shown in FIG. 1A. The PokitDok Scheduling Interface 110 may be REST based, interacting with resources as defined through URLs using HTTP Methods such as GET, POST, PUT, etc. FIG. 2A illustrates an example of a list supported scheduling systems operation that lists the PM scheduling systems supported within the PokitDok Scheduling Engine. FIG. 2B illustrates an example of a list appointment types operation that lists the system's appointment type ids and human readable descriptions. FIG. 2C illustrates an example of a list provider configurations operation that returns the configuration information associated with a registered healthcare provider as shown in the response in FIG. 2C. FIG. 2D illustrates an example of a provider Registration and Updates operation that registers a provider with the PokitDok Scheduling System. If the provider is already registered, the provider is updated.

FIG. 2E illustrates an example of a create an appointment slot operation that creates one or more open appointment slots on a provider's schedule. FIG. 2F illustrates an example of a query appointments operation that queries for a provider's appointments, using the provider's PokitDok provider id. As shown in FIG. 2F, this operation may have several query parameters as shown. FIGS. 2G and 2H illustrates an example of a reserve appointment(s) at a specific provider location given open slot id(s) operation. FIG. 2I illustrates an example of an update an appointment operation that changes attributes of appointment(s) given the appointment id(s). FIG. 2J illustrates an example of cancel an appointment operation that is used to cancel appointment(s) given the appointment id(s).

Figure 3C:
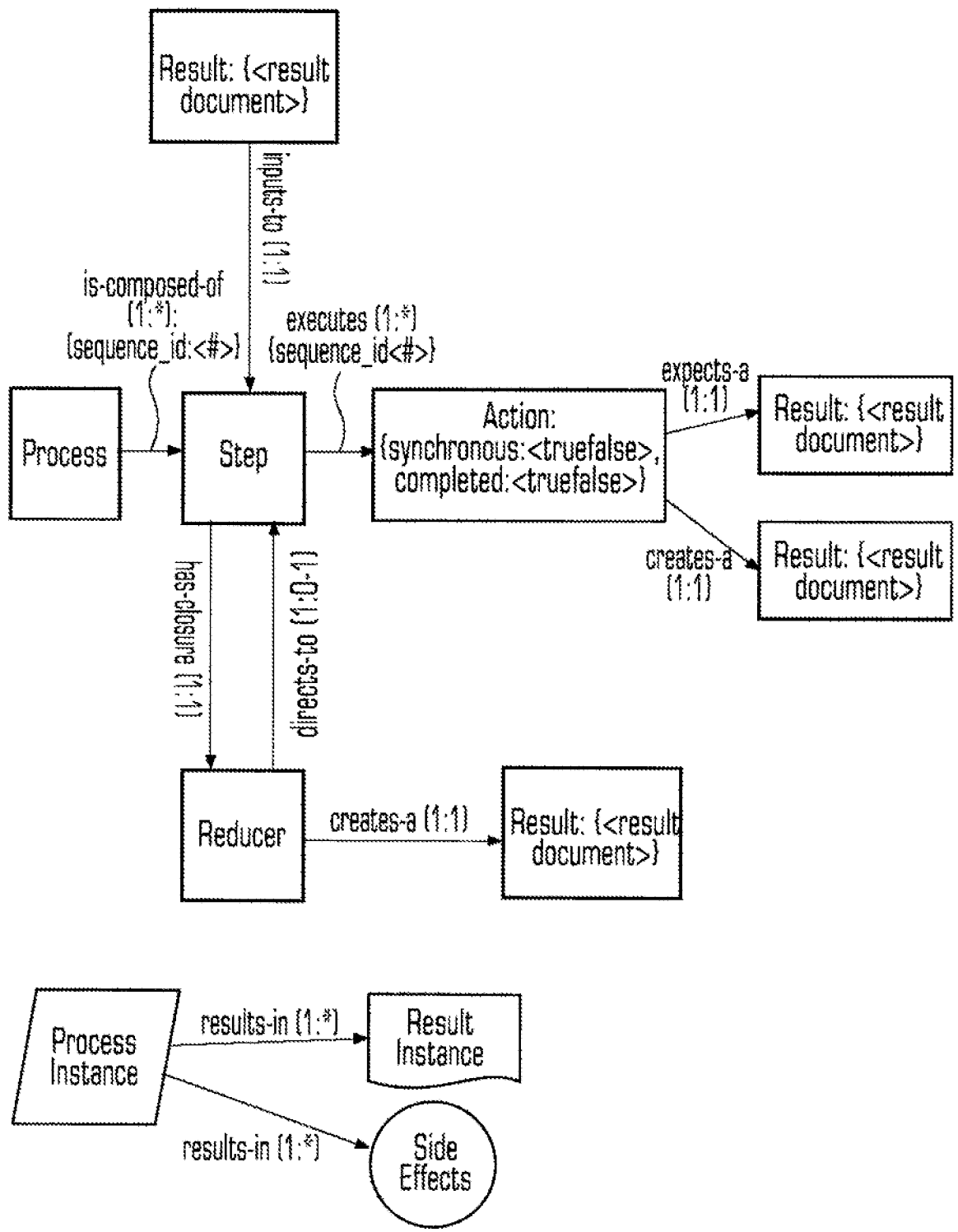

FIGS. 3A-3C illustrate a workflow vocabulary of a scheduling method that may be implemented in the workflow engine 116 in FIG. 1. The workflow engine 116 creates a workflow process using rule sets loaded from the rules repository. FIG. 3A shows examples of the different objects that may be part of the workflow engine. A workflow process is comprised of linear steps which execute one or more actions, that in turn, yield a result. A step's actions may execute in a synchronous or asynchronous manner. The reducer component monitors a step's execution, and "reduces" a step's result(s) into a single result when each of the step's actions have completed processing. If the workflow process contains additional steps, the reducer result is provided as input to the next step. If the workflow process does not contain additional steps, the reducer result is returned to the scheduling application through the PokitDok Scheduling Interface. FIGS. 3B and 3C illustrate the different objects of the workflow process and their relationships with each other.

The table below outlines how an input request from the scheduling interface is mapped to specific scheduling adapter operations, using the workflow engine within the PokitDok Scheduling Engine.

| Process Description | Process Action |
|---|---|
| An external client sends a request to the PokitDok Scheduling Interface, requesting an open appointment listing for a provider with a PokitDok ID = 1234 | /schedule/appointments/1234?booked=False &appointment_type=general &start_date=20141015 &end_date=20141016 |
| The Workflow Engine uses the rules repository to locate the Scheduling Adapter. | scheduling_adapter = f(provider identifier) |
| The Workflow Engine queries the rules repository and locates the rules set associated with the scheduling operation. | "Get_Availability Rules" Executes the Query_Slots action. Creates and returns the Open_Slots result |
| The Workflow Engine maps the rules set to the scheduling adapter operations, creating a workflow process. | scheduling_adapter_operation = f(scheduling_adapter, workflow process) |
| The workflow process is executed and returns a result. | [{   location: < >,   pd_provider_id: < PokitDok provider id for location >,   [slot: {     id: < >,     pd_provider_id: < PokitDok provider id for open slot >,     timespan: < >   }] }] |

FIGS. 4A-4E illustrate a method for scheduling a single appointment workflow that may be implemented by the system in FIGS. 1A and 1B. FIG. 4A illustrates the workflow process used to schedule a single appointment with a healthcare provider. FIG. 4A depicts the rule set metadata used to construct a workflow for scheduling a single appointment. The metadata is modeled as a DAG (Directed Acyclic Graph), which lends itself to modeling workflow processes. A traversal within a DAG has a clear starting and ending node, since a DAG traversal does not support looping back to its starting node or vertex. This aligns with a linear workflow process that has a defined beginning and ending step. The general form of the DAG can be formulated specifically within the areas of calculating flows. This can be further formulated specifically as, what is known in the vernacular as, PERT (Program Evaluation and Review Technique) or as CPM (Critical Path Method) functionalities. Details of these techniques may be found in "Introduction to Operations Research", F. Hillier & G. Lieberman, McGraw Hill (2001) that is incorporated herein by reference. Within the area of Directed Acyclic Graphs the techniques are to optimize the flow of the network such that the optimal scheduled event is selected from a set of suggested appointments based on the aforementioned criteria. For clarification, a Directed Acyclic Graph is depicted as:

$$G = \{V, E, t\}$$

where:
V=the vertex of the graph
E=the respective edge of the graph
t=the time base of the graph as it evolves The graph G is a function of the query mechanism of the system whereas:

$$f(x) \leftarrow G(V, E, t)$$

f(x) can be expressed as queries with respect to f(AppointmentTime, timespan, geolocation) as well as f(Speciality/Procedure, timespan, geoloc).

The nodes within the graph (G) represent workflow objects such as Process, Step, Action, Result, and Reducer. The functional representations allow for dynamic mapping of these attributes from based on the workflow engine. The rules are dynamically allocated with respect to the graph G. The directed edges within the graph, clearly define the predecessor and successor nodes in each adjacent vertex pair. For example the nodes Get_Providers and Query_Providers are adjacent to one another, connected by the executes relationship. The "executes" relationship is a directed relationship, originating with Get_Providers and ending with Query_Providers. This structure allows the processing step to be clearly stated as "the step Get_Providers executes the action Query_Providers".

An additional benefit of modeling rule set metadata using a DAG, is that the rule set may be updated independently of the workflow engine, allowing the workflow process to be dynamic.

FIGS. 4B and 4.C list a workflow vocabulary term applied to each graph node. Finally, FIGS. 4D and 4E provide a table of nodes and relationships depicted in FIG. 4A.

FIG. 5 illustrates a multiple appointment booking graph model that may be implemented by the system in FIGS. 1A and 1B. The workflow process is an aggregate process, as it consists of one or more instances of the Book_Appointment workflow process.

FIG. 6 illustrates an example of a workflow for scheduling an appointment and the data exchange during such a scheduling of the appointment. As shown in FIG. 6, the patient, a scheduling application API (on the computing device being used by the patient), the scheduling system 102 and the external scheduling system 104A-N interact with each other to schedule the appointment. Thus, the sequence of interactions of a patient with a scheduling application that utilizes the PokitDok Scheduling System and the interactions of the PokitDok Scheduling System internally and with the external scheduling systems to book appointments is shown in FIG. 6. As shown in FIG. 6, the workflow begins when the patient sets the schedule preferences (such as day/time, location and appointment type) for the particular appointment to be scheduled for the patient using the scheduling application user interface (that may be displayed on the computing device used by the patient to schedule the appointment. The scheduling system 102 may then save those schedule preferences. During the scheduling of an appointment, the one or more external scheduling systems 104A-N may set and save schedule preferences to the scheduling system 102.

The scheduling system 102 may then, for each provider's external system 104A-N get open appointment slots using the API of each particular external system 104A-N. This process may be operated in a loop so that the open slots for the different external systems 104A-N are being regularly determined. Then, the scheduling system 102, for each patient schedule preference, query for provider appointment matches in order to precedence. This process also may be operated in a loop so that matching slots are located. When a match is found (such as matching day/time, location and appointment type), the scheduling application user interface is notified of the match which is they displayed to the patient. The patient may then confirm the schedule match and book the appointment with the scheduling system 102 that in turn books the particular appointment for the patient with the external system 104A-N using the APIs of the external system. Using this workflow, the scheduling system 102 is thus able to schedule a patient appointment with a plurality of different external systems 104A-N that have different data formats, etc.

FIG. 7 illustrates an example of a workflow for scheduling multiple appointments that has the same elements interacting with each other. The workflow for multiple appointments may be the same as when scheduling a single appointment, but that workflow may be used repeatedly to schedule multiple dependent appointments, and expanded by considering all dependencies simultaneously in the matching of patient and provider scheduling preferences and dependencies, this process is shown in FIG. 7.

FIG. 8 illustrates an example of a workflow for updating an appointment. As shown in FIG. 8, an update from the patient is fed through the scheduling system 102 to the external system 104A-N to update an appointment. FIG. 9 illustrates an example of a workflow for cancelling an appointment. As shown in FIG. 9, a cancellation of an appointment from the patient is fed through the scheduling system 102 to the external system 104A-N to cancel the appointment.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include an/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

The invention claimed is:

1. A healthcare scheduling system, comprising:
    a computer system;
    a plurality of schedulers external to the computer system and connected to the computer system by a computer network;
    a scheduling interface that is part of the computer system and exchanges a plurality of pieces of data from the plurality of schedulers wherein each scheduler has its own application programming interface and data format for scheduling data;
    a scheduling system that is part of the computer system and schedules an appointment with a particular one of the plurality of schedulers, the scheduling system having a plurality of scheduling adapters wherein each scheduling adapter interfaces with a particular scheduler using the application programming interface and data format of the particular scheduler and a graph database having a set of rules wherein each rule defines a scheduling process for a particular scheduler;
    wherein the scheduling system receives scheduling data from each of the plurality of schedulers using the scheduler interface and selects a particular scheduling adapter and a particular rule for each particular scheduler; and
    wherein the scheduling system, using the selected particular scheduling adapter and the particular rule, retrieves open slots for the appointment from the plurality of schedulers, matches a set of schedule preferences from the appointment against the retrieved open slots from the plurality of schedulers to generate at least one matching open slot and generates an appointment request for the appointment for the matching open slot, converts the appointment request into a request for the particular one of the plurality of schedulers, the request conforming to the application programming interface and data format of the particular one of the schedulers.

2. The system of claim 1 further comprising a computing device that couples to and interacts with the scheduling system to schedule the appointment using the scheduling system.

3. The system of claim 2, wherein the scheduler system receives the appointment request from the computing device for the appointment for a particular provider that uses the particular scheduler and executes a workflow to schedule the appointment for the particular provider that uses the particular scheduler.

4. The system of claim 3, wherein the scheduler system locates a rule set for scheduling the appointment with a particular provider that uses the particular scheduler and uses the located rule set to schedule the appointment for the particular provider that uses the particular scheduler.

5. The system of claim 4, wherein the scheduler system generates the workflow based on the rule set for scheduling the appointment for the particular provider that uses the particular scheduler.

6. The system of claim 5, wherein the rule set is modeled using a graph.

7. The system of claim 6, wherein the graph is a directed acyclic graph.

8. The system of claim 7, wherein each node of the directed acyclic graph is a workflow object.

9. The system of claim 1, wherein the appointment request is one of a request to modify an existing appointment, a request to make a new appointment and a request to cancel an existing appointment.

10. A healthcare method for scheduling an appointment using a computer system, the method comprising:
    exchanging, using a scheduling interface that is part of the computer system, a plurality of pieces of data from a plurality of schedulers wherein each scheduler has its own application programming interface and data format for scheduling data;
    scheduling, using a scheduling system that is part of the computer system, the scheduling system having a plurality of scheduling adapters wherein each scheduling adapter interfaces with a particular scheduler using the application programming interface and data format of the particular scheduler and a graph database having a set of rules wherein each rule defines a scheduling process for a particular scheduler, an appointment with a particular one of the schedulers;
    receiving scheduling data from each of the plurality of schedulers using the scheduler interface;
    selecting a particular scheduling adapter and a particular rule for each particular scheduler;
    retrieving open slots for the appointment from the plurality of schedulers;
    matching a set of schedule preferences from the appointment against the retrieved open slots from the plurality of schedulers to generate at least one matching open slot;
    generating, by the scheduling system, an appointment request for the appointment for the matching open slot; and
    converting the appointment request into a request for the particular one of the plurality of schedulers, the request conforming to the application programming interface and data format of the particular one of the schedulers.

11. The method of claim 10 further comprising receiving, for a computing device of a user, the appointment request for the appointment for a particular provider that uses the particular scheduler and executing a workflow to schedule the appointment for the particular provider that uses the particular scheduler.

12. The method of claim 11 further comprising locating a rule set for scheduling the appointment with a particular provider that uses the particular scheduler and using the located rule set to schedule the appointment for the particular provider that uses the particular scheduler.

13. The method of claim 12 further comprising generating the workflow based on the rule set for scheduling the appointment for the particular provider that uses the particular scheduler.

14. The method of claim 13, wherein the rule set is modeled using a graph.

15. The method of claim 14, wherein the graph is a directed acyclic graph.

16. The method of claim 15, wherein each node of the directed acyclic graph is a workflow object.

17. The method of claim 10, wherein the appointment request is one of a request to modify an existing appointment, a request to make a new appointment and a request to cancel an existing appointment.

* * * * *